US00PP20747P2

(12) United States Plant Patent
Miyazaki

(10) Patent No.: US PP20,747 P2
(45) Date of Patent: Feb. 9, 2010

(54) ***MECARDONIA* PLANT NAMED 'SUNMECAKIRA'**

(50) Latin Name: *Mecardonia hybrida*
Varietal Denomination: Sunmecakira

(75) Inventor: Kiyoshi Miyazaki, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/290,135

(22) Filed: Oct. 28, 2008

(51) Int. Cl.
*A01H 5/00* (2006.01)

(52) U.S. Cl. ..... Plt./263.1
(58) Field of Classification Search ..... Plt./263, Plt./263.1
See application file for complete search history.

*Primary Examiner*—Susan B McCormick Ewoldt
(74) *Attorney, Agent, or Firm*—C. A. Whealy

(57) ABSTRACT

A new and distinct cultivar of *Mecardonia* plant named 'Sunmecakira', characterized by its compact, mounding and trailing plant habit; freely branching habit; dense and bushy growth habit; early and freely flowering habit; long flowering period; large bright yellow-colored flowers; and relative tolerance to high temperatures.

1 Drawing Sheet

Botanical designation: *Mecardonia hybrida.*
Cultivar denomination: 'Sunmecakira'.

BACKGROUND OF THE INVENTION

The present invention relates to a new and distinct cultivar of *Mecardonia* plant, botanically known as *Mecardonia hybrida,* and hereinafter referred to by the name 'Sunmecakira'.

The new *Mecardonia* plant is a product of a planned breeding program conducted by the Inventor in Higashiomi, Shiga, Japan. The objective of the breeding program is to create new freely branching compact *Mecardonia* cultivars with large flowers and high temperature tolerance.

The new *Mecardonia* plant originated from a cross-pollination made by the Inventor in Higashiomi, Shiga, Japan in 2004 of a proprietary selection of *Mecardonia hybrida* identified as code number 3Mec-8A, not patented, as the female, or seed, parent with a proprietary selection of *Mecardonia hybrida* identified as code number 01T-9, not patented, as the male, or seed, parent. The new *Mecardonia* was discovered and selected by the Inventor as a single flowering plant from within the progeny of the stated cross-pollination in a controlled greenhouse environment in Higashiomi, Shiga, Japan in 2006.

Asexual reproduction of the new *Mecardonia* plant by vegetative cuttings in a controlled environment in Higashiomi, Shiga, Japan since October, 2006, has shown that the unique features of this new *Mecardonia* are stable and reproduced true to type in successive generations.

SUMMARY OF THE INVENTION

Plants of the new *Mecardonia* have not been observed under all possible environmental conditions. The phenotype may vary somewhat with variations in environment such as temperature and light intensity, without, however, any variance in genotype.

The following traits have been repeatedly observed and are determined to be the unique characteristics of 'Sunmecakira'.

These characteristics in combination distinguish 'Sunmecakira' as a new and distinct cultivar of *Mecardonia:*

1. Compact, mounding and trailing plant habit.
2. Freely branching habit; dense and bushy growth habit.
3. Early and freely flowering habit.
4. Long flowering period.
5. Large bright yellow-colored flowers.
6. Relatively tolerant to high temperatures.

In side-by-side comparisons conducted in Higashiomi, Shiga, Japan, plants of the new *Mecardonia* differed from plants of the female parent selection in the following characteristics:

1. Plants of the new *Mecardonia* were more compact than plants of the female parent selection.
2. Plants of the new *Mecardonia* had larger flowers than plants of the female parent selection.

In side-by-side comparisons conducted in Higashiomi, Shiga, Japan, plants of the new *Mecardonia* differed from plants of the male parent selection in the following characteristics:

1. Plants of the new *Mecardonia* were larger than plants of the male parent selection.
2. Plants of the new *Mecardonia* had smaller flowers than plants of the male parent selection.

Plants of the new *Mecardonia* can be compared to plants of *Mecardonia* 'USMECA67', disclosed in U.S. Plant Pat. No. 15,777. In side-by-side comparisons conducted in Shiga, Japan, plants of the new *Mecardonia* differed from plants of 'USMECA67' in the following characteristics:

1. Plants of the new *Mecardonia* were more compact than plants of 'USMECA67'.
2. Plants of the new *Mecardonia* had smaller leaves than plants of 'USMECA67'.
3. Plants of the new *Mecardonia* flowered earlier than plants of 'USMECA67'.

BRIEF DESCRIPTION OF THE PHOTOGRAPHS

The accompanying photographs illustrate the overall appearance of the new *Mecardonia.* These photographs show the colors as true as it is reasonably possible to obtain in colored reproductions of this type. Colors in the photographs may differ slightly from the color values cited in the detailed botanical description which accurately describe the colors of the new *Mecardonia*.

The photograph at the top of the sheet comprises a side perspective view of a typical flowering plant of 'Sunmecakira' grown in a container.

The photograph at the bottom of the sheet is a close-up view of typical flowers and leaves of 'Sunmecakira'.

DETAILED BOTANICAL DESCRIPTION

The aforementioned photographs and following observations, measurements and values describe plants grown in Higashiomi, Shiga, Japan, under commercial practice during the late spring in an outdoor nursery. During the production of the plants, day temperatures averaged 23° C. and night temperatures averaged 12° C. Plants had been growing for four and five months when the description and photographs, respectively, were taken. In the following description, color references are made to The Royal Horticultural Society Colour Chart, 2001 Edition, except where general terms of ordinary dictionary significance are used.

Botanical classification: *Mecardonia hybrida* 'Sunmecakira'.

Parentage:

*Female, or seed, parent.*—Proprietary selection of *Mecardonia hybrida* identified as code number 3Mec-8A, not patented.

*Male, or pollen, parent.*—Proprietary selection of *Mecardonia hybrida* identified as code number 01T-9, not patented.

Propagation:

*Type.*—By vegetative cuttings.

*Time to initiate roots.*—About one week at 18° C. to 22° C.

*Time to produce a rooted cutting.*—About three weeks at 20° C. to 25° C.

*Root description.*—Fibrous, white in color.

*Rooting habit.*—Freely branching; moderately dense.

Plant description:

*Plant form/growth habit.*—Compact, mounding and trailing plant habit. Strong and vigorous growth habit.

*Plant height.*—About 9.7 cm.

*Plant diameter or spread.*—About 33.9 cm.

*Lateral branches.*—Quantity per plant: Freely branching habit with about 27 lateral branches developing per plant; dense and bushy growth habit. Length: About 19 cm. Diameter: About 1.2 mm. Internode length: About 1.7 cm. Texture: Smooth, glabrous. Color: Close to 146C.

Foliage description:

*Arrangement.*—Opposite, simple.

*Length.*—About 1.9 cm.

*Width.*—About 0.9 cm.

*Shape.*—Ovate.

*Apex.*—Acute.

*Base.*—Obtuse.

*Margin.*—Serrate.

*Texture, upper and lower surfaces.*—Pubescent.

*Venation pattern.*—Pinnate; reticulate.

*Color.*—Developing and fully expanded leaves, upper surface: Close to 137B; venation, close to 144B. Developing and fully expanded leaves, lower surface: Close to 138B; venation, close to 144B.

*Petiole length.*—About 1.1 mm.

*Petiole diameter.*—About 1.9 mm.

*Petiole texture, upper and lower surfaces.*—Smooth, glabrous.

*Petiole color, upper and lower surfaces.*—Close to 144B.

Flower description:

*Flower arrangement and habit.*—Solitary axially flowers that face mostly upward or outward. Freely flowering habit with about 95 open flowers per plant at one time. Early flowering; plants begin flowering about three to four weeks after planting.

*Natural flowering season.*—Long flowering period; spring until late autumn in Japan; flowering continuous during this period.

*Flower longevity on the plant.*—About five days; flowers persistent.

*Fragrance.*—None detected.

*Flower size.*—About 1.7 cm by 1.5 cm.

*Flower depth (height).*—About 1.4 cm.

*Flower buds.*—Length: About 1.1 cm. Diameter: About 3 mm. Shape: Ellipsoidal. Color: Close to 10A.

*Corolla.*—Arrangement: Single whorl of four petals; petals fused at the base. Petal length, upper petal: About 6.7 mm. Petal length, lateral petals: About 6.1 mm. Petal length, lower petal: About 7.1 mm. Petal width, upper petal: About 1 cm. Petal width, lateral petals: About 6.7 mm. Petal width, lower petal: About 8.8 mm. Petal shape, upper petal: Broadly obovate. Petal shape, lateral and lower petals: Cordate. Petal apex, upper petal: Slightly emarginate. Petal apex, lateral petals: Cordate to truncate. Petal apex, lower petal: Cordate. Petal margin, all petals: Entire. Petal texture, upper and lower surfaces, all petals: Smooth, glabrous. Color: Upper and lateral petals, when opening and fully opened, upper surface: Close to 9A; lines towards the base, close to 187A. Upper and lateral petals, when opening and fully opened, lower surface: Close to 9C. Lower petals, when opening and fully opened, upper surface: Close to 9A. Lower petals, when opening and fully opened, lower surface: Close to 9C. Throat: Close to 157A; lines, close to 187A. Tube: Close to 157A.

*Calyx.*—Quantity per flower: Two sepals. Sepal length: About 9.7 mm. Sepal width: About 1.4 mm. Sepal shape: Lanceolate. Sepal apex: Acute. Sepal base: Obtuse. Sepal margin: Entire. Sepal texture, upper and lower surfaces: Smooth, glabrous. Sepal color, upper and lower surfaces: Close to 144B.

*Flower bracts.*—Arrangement: A single whorl of three bracts. Length: About 1.1 cm. Width: About 8 mm. Shape: Ovate. Apex: Acute. Base: Obtuse. Margin: Entire. Texture, upper and lower surfaces: Smooth, glabrous. Color, upper and lower surfaces: Close to 144A to 144B.

*Peduncles.*—Length: About 4.2 cm. Diameter: About 6 mm. Texture: Smooth, glabrous. Color: Close to 166A.

*Reproductive organs.*—Stamens: Quantity per flower: Four. Anther shape: Globose. Anther size: About 1.4 mm by 1.2 mm. Anther color: Close to 157D. Pollen amount: Scarce. Pollen color: Close to 157D. Pistils: Quantity per flower: One. Pistil length: About 4.6 mm. Style color: Close to 145B. Stigma shape: Ellipsoidal. Stigma color: Close to 145B. Ovary color: Close to 145B. Seed/fruit: Seed and fruit production has not been observed.

Disease/pest resistance: Plants of the new *Mecardonia* have not been shown to be resistant to pathogens and pests common to *Mecardonia*.

Temperature tolerance: Plants of the new *Mecardonia* have been observed to tolerate temperatures ranging from about 0° C. to about 35° C.

It is claimed:

1. A new and distinct *Mecardonia* plant named 'Sunmecakira' as illustrated and described.

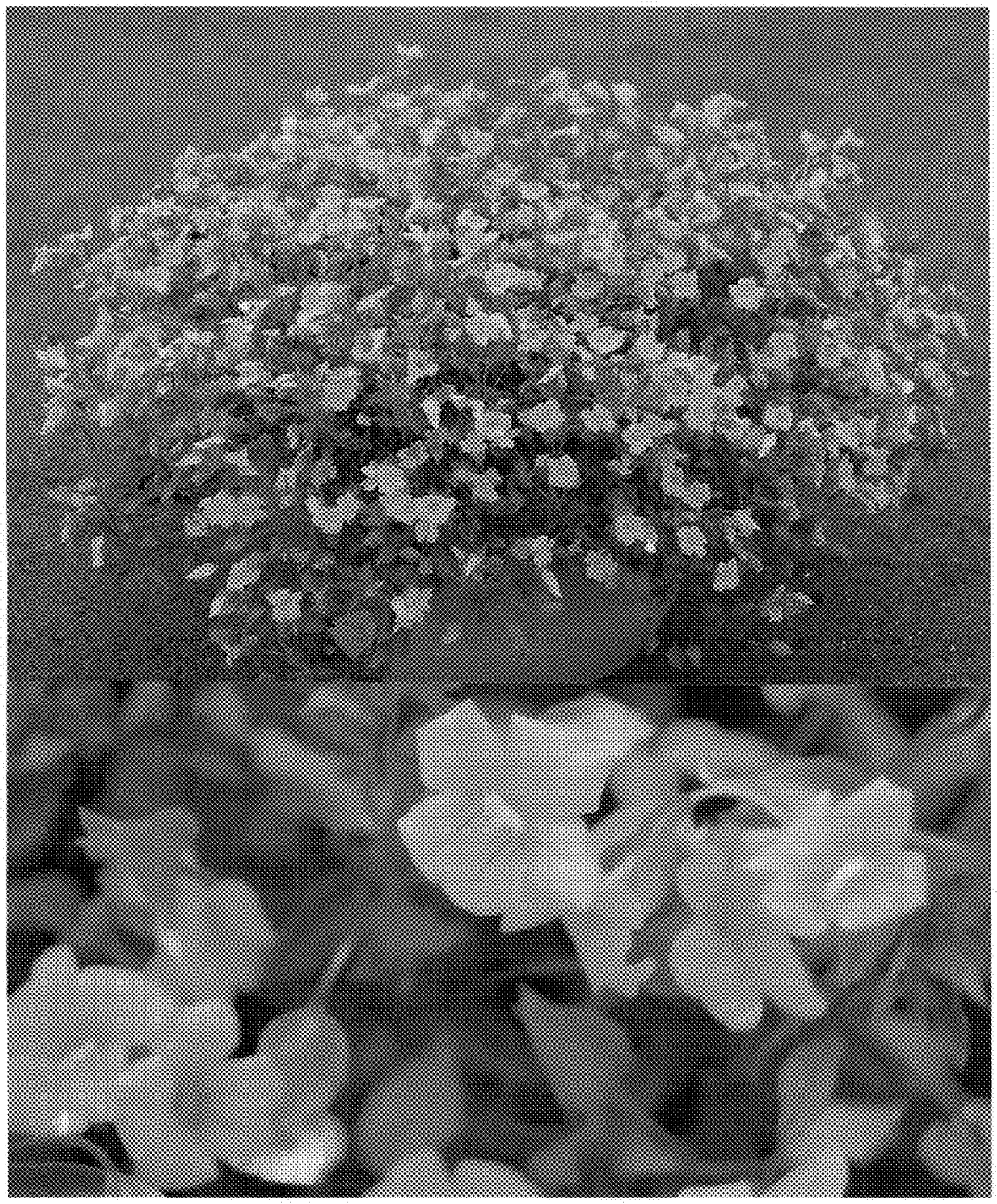

* * * * *